(12) United States Patent
Forsell

(10) Patent No.: US 8,398,710 B2
(45) Date of Patent: Mar. 19, 2013

(54) BREAST IMPLANT SYSTEM

(75) Inventor: Peter Forsell, Baar (CH)

(73) Assignee: Milux Holding SA, Luxembourg (LU)

( * ) Notice: Subject to any disclaimer, the term of this patent is extended or adjusted under 35 U.S.C. 154(b) by 153 days.

(21) Appl. No.: 12/865,306

(22) PCT Filed: Jan. 30, 2009

(86) PCT No.: PCT/EP2009/000622
§ 371 (c)(1),
(2), (4) Date: Oct. 21, 2010

(87) PCT Pub. No.: WO2009/095259
PCT Pub. Date: Aug. 6, 2009

(65) Prior Publication Data
US 2011/0054606 A1    Mar. 3, 2011

Related U.S. Application Data

(60) Provisional application No. 61/006,807, filed on Jan. 31, 2008.

(51) Int. Cl.
*A61F 2/12* (2006.01)
(52) U.S. Cl. .......................................................... 623/8
(58) Field of Classification Search .................. 623/7–8; 606/192
See application file for complete search history.

(56) References Cited

U.S. PATENT DOCUMENTS

| | | | |
|---|---|---|---|
| 3,683,424 A | 8/1972 | Pangman | |
| 4,217,889 A * | 8/1980 | Radovan et al. | 600/20 |
| 4,507,810 A | 4/1985 | Bartholdson | |
| 4,615,704 A | 10/1986 | Frisch | |
| 4,636,213 A | 1/1987 | Pakiam | |
| 4,662,357 A | 5/1987 | Pierce et al. | |
| 4,731,081 A | 3/1988 | Tiffany et al. | |
| 4,790,848 A | 12/1988 | Cronin | |
| 4,984,585 A | 1/1991 | Austad | |
| 5,146,933 A * | 9/1992 | Boyd | 128/899 |
| 5,236,454 A | 8/1993 | Miller | |
| 5,549,671 A | 8/1996 | Waybright | |

(Continued)

FOREIGN PATENT DOCUMENTS

| | | |
|---|---|---|
| WO | 2006/034273 | 3/2006 |
| WO | 2006/079905 A2 | 8/2006 |

(Continued)

OTHER PUBLICATIONS

International Search Report for PCT/EP2010/060078, mailed Sep. 3, 2010.

(Continued)

*Primary Examiner* — Suzette J Gherbi
(74) *Attorney, Agent, or Firm* — Nixon & Vanderhye PC

(57) ABSTRACT

A breast implant system is provided comprising a plurality of chambers including one or more first fluid chambers (1) and one or more second fluid chambers (2). The first fluid chamber (1) forms part of a breast implant (10), whereas the second fluid chamber (2) may also form part of the breast implant or may be implanted remote from the breast implant. The first and second fluid chambers are interconnected so as to allow exchange of fluid between the first and second chambers, thereby causing the shape and, depending upon the specific embodiment, also the volume to change accordingly.

20 Claims, 13 Drawing Sheets

U.S. PATENT DOCUMENTS

| | | | |
|---|---|---|---|
| 5,779,734 | A | 7/1998 | Ledergerber |
| 5,882,353 | A | 3/1999 | VanBeek et al. |
| 6,187,043 | B1 | 2/2001 | Ledergerber |
| 6,668,836 | B1 | 12/2003 | Greenburg et al. |
| 6,755,861 | B2 * | 6/2004 | Nakao ............................... 623/8 |
| 6,875,233 | B1 | 4/2005 | Turner |
| 7,081,136 | B1 | 7/2006 | Becker |
| 2001/0010024 | A1 * | 7/2001 | Ledergerber ............... 623/23.74 |
| 2002/0143396 | A1 | 10/2002 | Falcon et al. |
| 2003/0074084 | A1 * | 4/2003 | Nakao ......................... 623/23.67 |
| 2006/0069403 | A1 * | 3/2006 | Shalon et al. .................. 606/192 |
| 2006/0111791 | A1 | 5/2006 | Forsell |
| 2006/0235482 | A1 | 10/2006 | Forsell |
| 2009/0012372 | A1 * | 1/2009 | Burnett et al. ................ 600/300 |
| 2009/0192533 | A1 * | 7/2009 | Dlugos et al. ................. 606/157 |
| 2009/0210056 | A1 * | 8/2009 | Forsell ............................... 623/8 |
| 2009/0299473 | A1 | 12/2009 | Govrin-Yehudian et al. |
| 2011/0054606 | A1 | 3/2011 | Forsell |
| 2011/0196422 | A1 | 8/2011 | Forsell |
| 2011/0264213 | A1 * | 10/2011 | DeMiranda ....................... 623/8 |
| 2012/0022324 | A1 * | 1/2012 | Forsell ............................ 600/40 |

FOREIGN PATENT DOCUMENTS

| | | |
|---|---|---|
| WO | 2007/004213 | 1/2007 |
| WO | 2008/053630 A1 | 5/2008 |

OTHER PUBLICATIONS

International Search Report for PCT/EP2010/060079, mailed Nov. 23, 2010.
International Search Report for PCT/EP2009/000622, mailed Apr. 1, 2009.
Written Opinion of the international Searching Authority for PCT/EP2009/000622, mailed Apr. 1, 2009.
Office Action for U.S. Appl. No. 12/320,670, mailed Aug. 24, 2011.
Final Office Action U.S. Appl. No. 12/320,670, mailed Jan. 9, 2012.
Written Opinion of the International Searching Authority for PCT/EP2010/060079, mailed Nov. 23, 2010.
Written Opinion of the International Searching Authority for PCT/EP2010/060078, dated Sep. 3, 2010.

\* cited by examiner

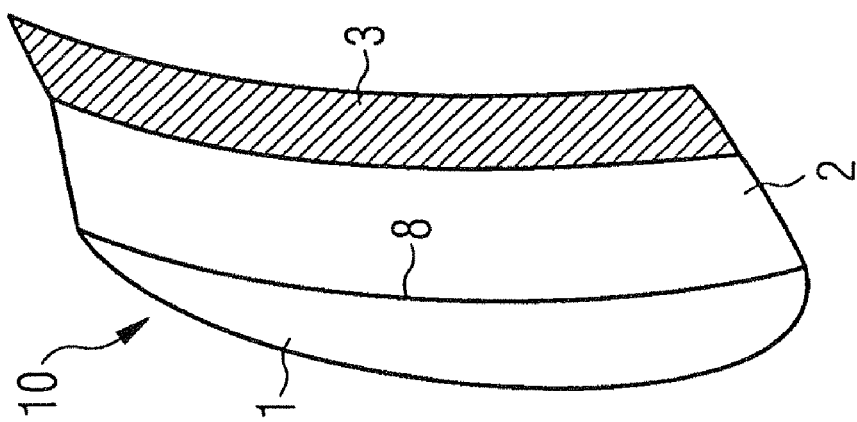
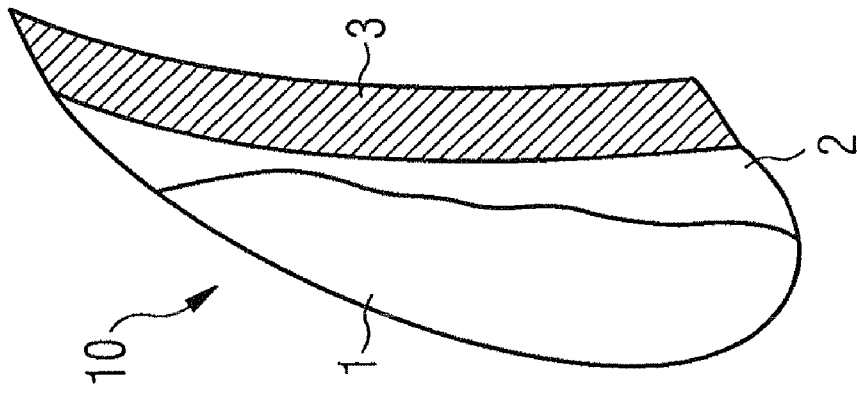
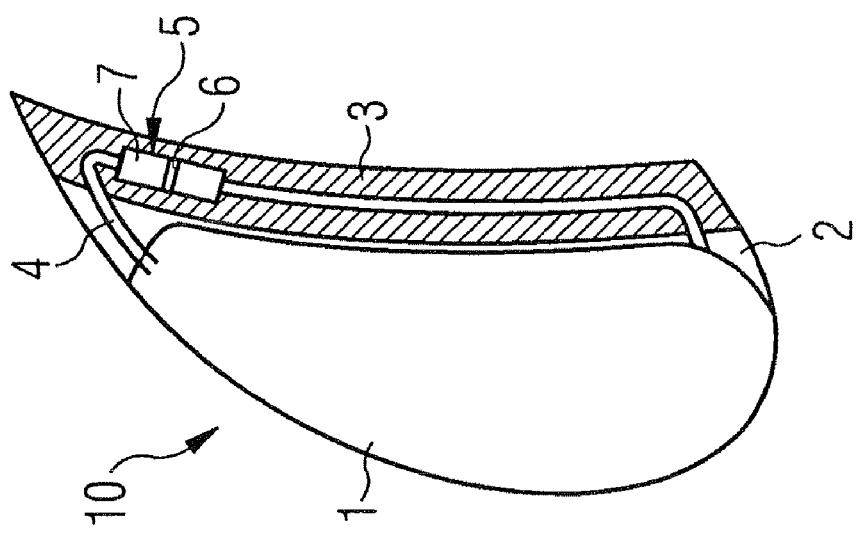

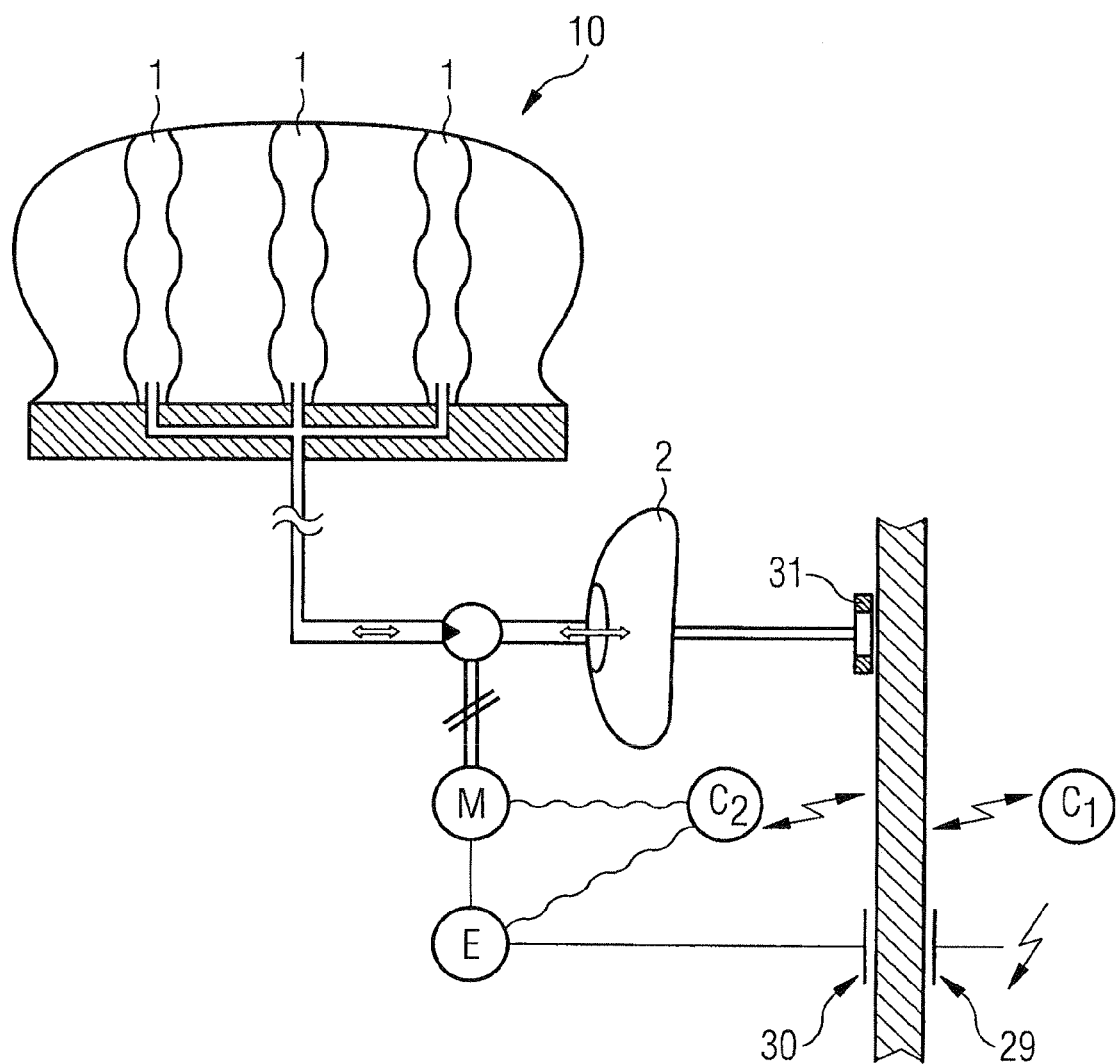

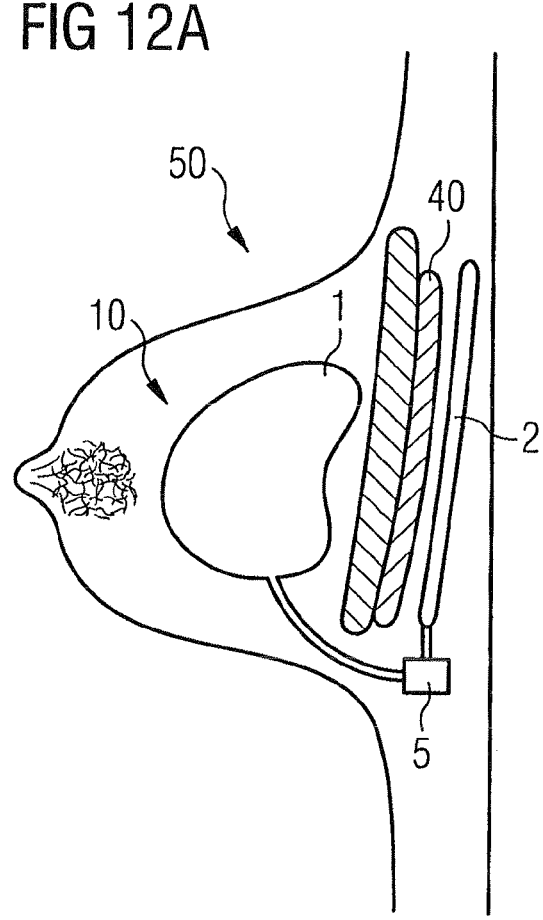
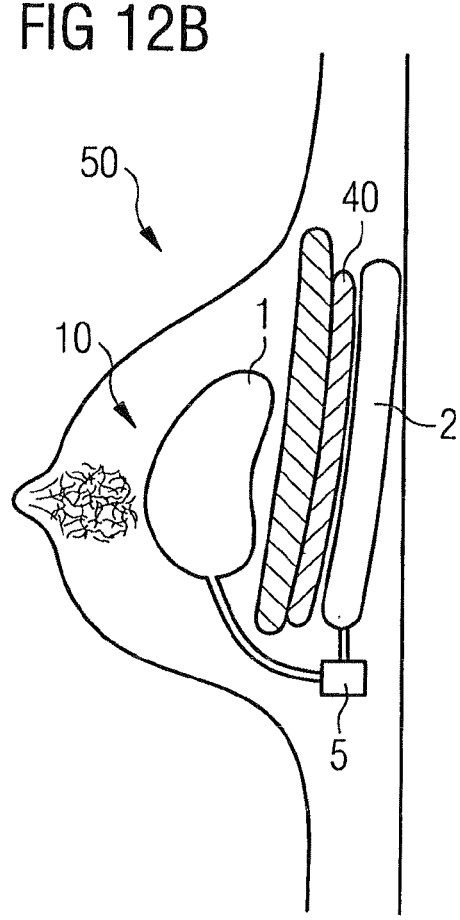
FIG 12A
FIG 12B

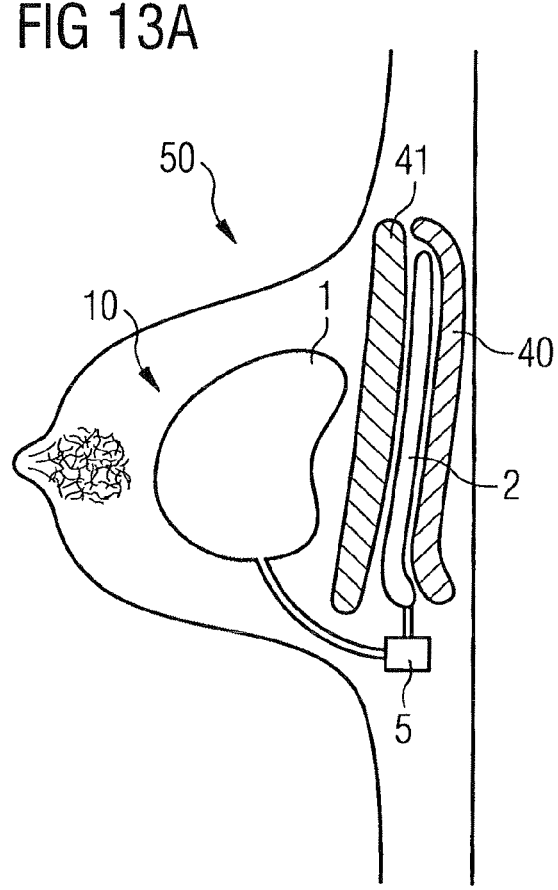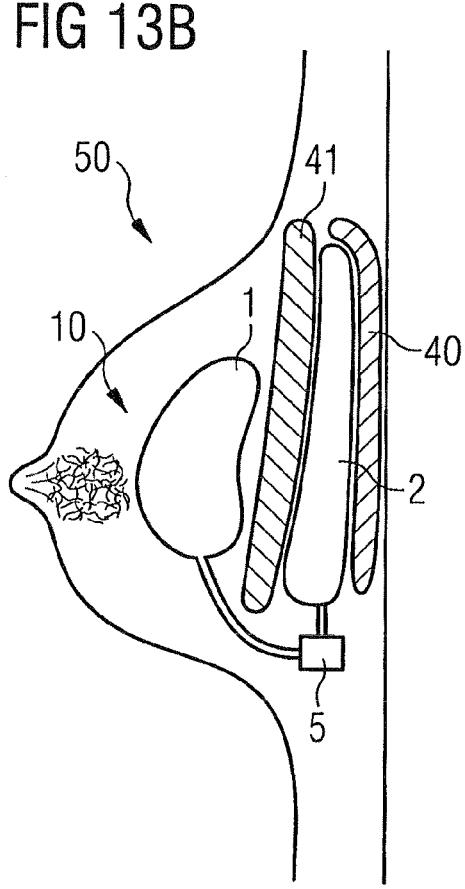

BREAST IMPLANT SYSTEM

This application is the U.S. national phase of International Application No. PCT/EP2009/000622, filed 30 Jan. 2009, which designated the U.S. and claims priority to U.S. Application No. 61/006,807, filed 31 Jan. 2008, the entire contents of each of which are hereby incorporated by reference.

BACKGROUND OF THE INVENTION

The present invention relates to a breast implant system which allows the shape of a breast implant to be varied after its implantation in the patient's body.

Breast implants are typically used to either replace a natural breast that has been removed, e.g. due to cancer, or to increase the size of a natural breast when the natural size is considered unsatisfactory. In general, people who desire to change the overall size and shape of their breast implants after implantation, have to undergo major surgery. It would be desirable that the patient can adjust the size and shape of the breast implant easily, depending on current needs. For instance, as time goes by, the patient might no longer be happy with the size and/or shape of the artificial breast. Or, the patient might want to change the shape or size only temporarily. For instance, one might wish to reduce the volume of the breast implant during sports activities or one might wish to enlarge the size for a particular event, such as a party or the like.

U.S. Pat. No. 6,875,233 B1 discloses a breast implant which allows the overall size and shape thereof to be changed once it has been surgically implanted. Such breast implant includes an exterior shell and an inner bladder. The exterior shell is typically a bellows having a plurality of pleats, so that the outer size of the implant is variable. As the bladder is filled, the exterior shell expands in a manner that creates a lifting effect and a ballooning effect. A valve connected to both the exterior shell and the inner bladder can be used to fill the bladder external to the patient without the need for further surgery after the implant has been implanted in the patient. The bladder may be filled with a liquid, a gas or a solid, and such filler can be added and removed through the valve as needed. The valve either remains external, so that it can be used without any further surgery, or it can be located under the patient's skin, in which case minor surgery must be performed to access the valve.

The options for changing the shape of this prior art breast implant are limited. Also, it is inconvenient for the patient that the valve for accessing the inner bladder of the breast implant permanently penetrates the patient's skin or, where it is implanted subcutaneously, requires minor surgery to be accessed.

SUMMARY OF THE INVENTION

It is therefore a primary object of the present invention to provide breast implants or, more specifically, a breast implant system, that offers new possibilities for varying the shape of the breast implant after implantation.

A breast implant system according to the present invention comprises a plurality of chambers, including one or more first fluid chambers and one or more second fluid chambers. At least the first fluid chambers are to be implanted in the human body to form part of a breast implant. The second fluid chambers are either implanted also to form part of the breast implant, or are implanted inside the patient's body remote from the breast implant. The first fluid chambers are interconnected with the second fluid chambers, such that fluid can be exchanged between the first and second fluid chambers, so as to change their respective fluid content. In specific embodiments, further (third) chambers can be present, which may or may not be in fluid connection with the first or/and second fluid chambers and which need not necessarily contain any fluid but may even contain non-flowing material.

A fluid in the sense of the present invention encompasses any flowable material that can be exchanged between the first and second fluid chambers, in particular a gas, a liquid, a gel, a flowable foam or any combination thereof.

The exchange of fluid between the first and second implanted fluid chambers, resulting in a change of the respective fluid content in the fluid chambers, allows the shape of the breast implant to be varied without the need to administer or remove any fluid through the patient's skin. This is very convenient for the patient, as there is no valve sticking out through the skin and there is no need to perform minor surgery for accessing any valve located underneath the skin. This does not preclude there also being provided in the present invention an injection port arranged subcutaneously in order to refill the content of any of the chambers or to release any excess fluid, should need arise.

It is thus possible to implant the breast implant system of the present invention completely in the patient's body (apart from any external wireless remote control elements, if present, as will be described below).

As mentioned above, one or more of the second fluid chambers or even all chambers of the breast implant system may form part of the breast implant. Thus, according to a preferred embodiment, the shape of the breast implant can be changed without changing the overall volume of the breast implant, namely in the case where a second fluid chamber forms part of the breast implant along with the first fluid chamber, and fluid is exchanged between this second fluid chamber and the first fluid chamber. For instance, the patient may simply compress one of the fluid chambers within the breast implant from outside the breast to urge fluid to flow into a neighboring fluid chamber within the breast implant, and vice versa, until achieving a proper fluid distribution among the various fluid chambers so as to give the breast implant the personally most preferred shape.

One or more third fluid chambers may further be provided in the breast implant to participate when fluid is exchanged between the first and second fluid chamber. For instance, the third fluid chamber may be interposed between the first and second fluid chambers and may comprise means, such as a pump, to support the fluid exchange between the first and second fluid chambers.

The first and second fluid chambers may be separated from one another by a non-stretchable wall, which can be flexible or rigid, but have stretchable exterior walls. The non-stretchable separating wall guarantees that upon compression of the chambers, fluid will flow from the compressed fluid chamber through the non-stretchable wall into an adjacent chamber with a stretchable exterior wall. Provided that the flow path between the two adjacent fluid chambers includes a valve which opens in the one and/or the other direction only when a predetermined pressure difference is exceeded, the non-stretchable separating wall hinders the high pressure in one chamber from being transmitted by the separating wall to the fluid in the adjacent chamber. Thus, it is possible to have different pressures in different fluid chambers. This way, the number of shape variations of the breast implant is increased.

According to other embodiments of the invention, not only the shape of the breast implant is varied but also the volume thereof. This can be achieved by adding fluid to or removing fluid from the first fluid chambers in the breast implant from outside the breast implant. In this case the mass of the breast implant changes. However, according to a specific embodiment of the present invention, the shape and also the volume of the breast implant are changed with the mass of the breast implant remaining constant. This can be achieved with different types of fluid in the fluid chambers, i.e. at least one fluid chamber comprising a compressible fluid and at least one other fluid chamber comprising an incompressible fluid. More specifically, the first fluid chamber within the breast implant may comprise an incompressible fluid and the second fluid chamber within the breast implant a compressible fluid, and a transfer of the incompressible fluid from the first fluid chamber to the second fluid chamber will result in an increase of pressure within the second fluid chamber and, thus, in a decrease of volume of the compressible fluid contained in the second fluid chamber. Again, this effect will be enhanced when a non-stretchable wall, which may be flexible or rigid, is arranged between the first and second chambers. More preferably, the non-stretchable wall may completely enclose the fluid chamber comprising the compressible fluid. For instance, the fluid chamber comprising the compressible fluid may be placed within the fluid chamber comprising the incompressible fluid.

When an incompressible fluid is transferred into the chamber comprising a compressible fluid, it may be difficult to ensure that upon the next shape variation of the breast implant only the incompressible fluid and no compressible fluid is moved back into the chamber with incompressible fluid. It is therefore preferred to provide the compressible fluid in an isolated chamber. In this case, both the first and second fluid chambers in the breast implant comprise an incompressible fluid and the exchange of the incompressible fluid between the first and second fluid chambers results in an increase of pressure within the third fluid chamber that also forms part of the breast implant and that is filled with the compressible fluid. Thus, the volume of the third fluid chamber will decrease accordingly, and so will the overall volume of the breast implant.

This way, the shape of the breast implant can be changed from flat to high and vice versa, this involving a volume change of the breast implant, while the weight of the breast implant is not affected.

Where at least one of the second fluid chambers is implanted remote from the breast implant in the patient's body, and where the shape of the breast implant is changed by exchanging fluid between the first fluid chamber or chambers in the breast implant and the remotely implanted second fluid chamber, such shape variation will involve a change of the breast implant's volume (and weight). Thus, the size of the breast implant will increase accordingly.

There may be one or more first fluid chambers provided in the breast implant and/or there may be one or more second fluid chambers remotely implanted. Each of the remotely implanted second fluid chambers can be connected to one or more of the first fluid chambers in the breast implant. Also, each of the first fluid chambers in the breast implant may be connected to one or more of the remotely implanted second fluid chambers. Depending on how the first and second fluid chambers are interconnected, a great variety of shape variations can be achieved with the breast implant system. One or more valves can be provided to control fluid flow between the fluid chambers.

Again, a third chamber isolated from the first and second fluid chamber can be provided and may have different functions. For instance, the third chamber may form part of the breast implant and may contain a compressible fluid, the arrangement being such that fluid exchange between the first and second fluid chambers containing an incompressible fluid results in a change of pressure within the at least one third chamber containing the compressible fluid, thereby causing a change of volume of the breast implant.

In another embodiment of the invention, the third chamber is a fluid chamber cooperating with the first and second fluid chambers such that when fluid is exchanged between the first and second fluid chambers the fluid in the third fluid chamber is caused to move, the amount of fluid moved in the third fluid chamber being different to the amount of fluid exchange between the first and second fluid chambers. This can also be referred to as a servo system.

According to one preferred embodiment of such servo system, the third fluid chamber comprises sub-chambers which are interconnected. At least one of the first and second fluid chambers is operatively connected to at least one of the sub-chambers and is adapted to expand this sub-chamber when fluid is exchanged between the first and second fluid chambers. Fluid will then flow between the sub-chambers into the expanded sub-chamber, and the amount of fluid flow can be substantially different to the amount of fluid exchange between the first and second fluid chambers. There are various alternative ways of realizing such servo system in the breast implant system of the present invention. In this context, it is preferable to provide a spring element to urge the third fluid chamber or at least one of the sub-chambers thereof into a state of minimum or maximum volume, i.e. into a normally small or a normally large state. Energy is then only needed to exchange fluid between the first and second fluid chambers in one direction, whereas the necessary force required to exchange the fluid in the opposite direction is provided by the spring force, which spring force can be released up to an appropriate amount according to the patient's preferences.

The servo system can be designed as a reverse servo system to the extent that only a little amount of fluid needs to be exchanged between the sub-chambers of the third fluid chamber in order to achieve a relatively large amount of fluid exchange between the first and second chambers. This means that a relatively large force but small stroke is needed to achieve the relatively large amount of fluid exchange between the first and second fluid chambers. This is particularly convenient where one of the sub-chambers of the third fluid chamber is provided for subcutaneous implantation so as to be manually compressible by the patient from the outside of the patient's body. Thus, the subcutaneously arranged compressible sub-chamber may have a relatively small volume and will therefore not adversely affect the patient's visual appearance, with the negative side effect that the patient will have to apply a relatively large force on the relatively small subcutaneous sub-chamber in order to achieve the desired, relatively large volume change in the breast implant.

In cases where the breast implant system does not include a servo system or, thus, any sub-chambers of any third fluid chamber, the remotely implantable second sub-chamber may itself be arranged for subcutaneous implantation so as to be operable by the patient from outside the patient's body.

Instead of any fluid chamber being arranged under the patient's skin for manual operation by the patient, it may be implanted deeper in the patient's body, such as in the patient's abdominal cavity or inside the patient's chest area, where it is preferably implanted outside the patient's thorax, in particular under the pectoralis muscle. In this context the breast implant system would comprise a pump for pumping the fluid between the fluid chambers inside the breast implant and those fluid chambers remote from the breast implant. Of course, a pump can also be useful in the case where fluid is exchanged between two or more fluid chambers inside the breast implant.

When implanting one or more of the second fluid chambers of the system under the pectoralis muscle, it may be implanted either underneath the patient's minor pectoralis muscle next to the patient's thorax or between the patient's minor and major pectoralis muscles. In either case, the second fluid chamber is preferably wide and flat as compared to the first fluid chamber of the breast implant, i.e. it has a substantially larger surface-to-volume ratio than the first fluid chamber. This way, a substantial subjective volume change of the patient's breast can be achieved by exchanging fluid between the first and second fluid chambers. The arrangement of the second fluid chamber between the major and minor pectoralis muscles can be more convenient for the patient as compared to the arrangement next to the patient's thorax.

According to a preferred aspect of the present invention, the breast implant is made to be light weight. Therefore, at least one of the plurality of chambers is at least partly filled with a gas or with another light weight material that has a density substantially lower than the density of water. The chamber filled with the light weight material need not necessarily be in fluid connection with the first and second fluid chambers. It may be isolated from the first and second fluid chambers, as in the previously mentioned embodiment with a fluid chamber comprising a compressible fluid.

Instead of a gas, a non-flowable foam may be provided, and the foam may be filled with gas. The non-flowable foam may likewise be filled with a material resembling human material, such as a collagen. Also, a part of the non-flowable foam may form closed cells which are preferably filled with gas or with another light weight material, such as collagen. Another part of the non-flowable foam may be an open cell foam which may be arranged to absorb at least part of the fluid to be exchanged between the first and second fluid chambers.

The chamber with the light weight material may also include a soft material, such as silicone or any other gel-like material, with bubbles dispersed therein. Again, the bubbles may be filled with a gas and/or material that resembles human material, such as collagen.

According to another aspect of the breast implant system, in order to provide stiffness giving the breast implant a basic contour which is maintained throughout any shape changes of the breast implant, a rigid back wall may be provided to be placed adjacent the patient's thorax. At least the first chamber forming part of the breast implant is fixedly connected to the rigid back wall. The first fluid chamber and the rigid back wall may together conveniently form an enclosed space.

Problems can arise with fibrosis forming on the outer surface of the breast implant. Such fibrosis becomes relatively strong and may obstruct volume changes of the breast implant. It is therefore preferable to design the breast implant such that the outer walls thereof do not change their outer surface area upon an increase or decrease of the breast implant's volume. For instance, the breast implant may have a flexible outer wall, which is preferably non-stretchable, and the flexible outer wall may be formed like a bowl, so that the shape of the bowl can be changed without changing the outer surface area thereof. Again, the flexible outer wall may be mounted on a stiff frame to guarantee a basic contour of the breast implant.

In a specific embodiment, the flexible outer wall is provided with one or more folds or pleats so as to allow a flexible movement of the outer wall by the folds or pleats being unfolded upon an increase of an inner volume of the breast implant. Since fibrosis tends to build up in the inner corners of a zig-zag-shaped wall, it is preferred that the folds—in cross section—comprise trapezoidal sections.

However, it is not excluded that the flexible outer wall is at least partly stretchable so as to allow, where possible, stretching of the outer wall upon an increase of an inner volume of the breast implant.

In order to improve the overall appearance of the breast implant, the part of the outer wall facing away from the patient's chest may comprise a compartment filled with a soft material, such as a foam or a silicone. This gives the breast implant the look and feel of a natural breast and can also serve to level out any unevenness caused by different fillings and/or different pressures in the breast implant's fluid chambers.

After a while it may become necessary to remove fluid from one or more of the fluid chambers or, more probably, to add fluid thereto. In particular when gas is contained in one or more of the fluid chambers, it is possible that part of the gas will get lost over time due to leakage. Therefore, in order to maintain a desired balance in the fluid chambers, the breast implant system according to a preferred embodiment includes at least one injection port for implantation under the patient's skin so as to allow fluid to be added to or removed from the fluid chambers by injection from outside the patient's body. Two or more injection ports may be provided and may be connected to the fluid chambers via individual fluid connections so as to allow fluid to be individually added to or removed from specific fluid chambers. The injection port or ports can further be used to adjust the pressure in the breast implant system. For instance, when a patient has achieved a particular distribution of fluid among the first and second fluid chambers that feels best, it is convenient for the patient to release any excess pressure from the system by selectively removing fluid from the system through the injection port or ports.

Alternatively, the pressure in the fluid chambers may be equalized using a pressure relief valve. Such pressure relief valve may be provided at least for controlling the pressure in one or more of the first fluid chambers forming part of the breast implant.

As mentioned above, a pump may be provided in the breast implant system for pumping fluid between the first and second fluid chambers. In this context, at least one reservoir—i.e. a third fluid chamber—may be provided remote from the breast implant and connected to the pump so as to allow fluid to be exchanged at least between the first and second fluid chambers by pumping fluid with said pump from the first fluid chamber into the reservoir and from the reservoir into the second fluid chamber, and vice versa. Alternatively, the pump may be arranged between the first fluid chambers in the breast implant and a remotely implanted second fluid chamber. Instead of the pump being provided outside the first and second fluid chambers, it may be contained within one of the first and second fluid chambers.

As mentioned above, the pump may also be implanted subcutaneously so as to be manually operable through the skin. In this case, a purely hydraulic or purely pneumatic pump may be used.

However, where the pump is not manually operable, the breast implant system may comprise at least one motor for automatically driving the pump. In this case, the pump may be of the hydraulic, pneumatic or mechanical type. Also, a manually operable switch for activating the motor may be arranged subcutaneously for operation by the patient from outside the patient's body.

The motor itself may be arranged to be driven by electric or electromagnetic energy, by an electric or magnetic pulsating field or by ultrasonic energy.

The breast implant system may further comprise an energy source for supplying the energy directly or indirectly to at least one energy consuming part of the system, in particular to the aforementioned motor for driving the pump. Such energy source may include energy storage means, such as a battery or an accumulator, in particular one or more of a rechargeable battery and a capacitor.

The energy source, when provided outside the patient's body, preferably comprises a wireless energy transmitter for wirelessly transmitting energy from outside the patient's body to the implanted energy storage means.

The breast implant system preferably further comprises an implantable energy transforming device for transforming wirelessly transmitted energy into electric energy. The electric energy is stored in the energy storage means and/or is used to drive the energy consuming part (motor and pump) as the energy transforming device transforms the wireless energy into the electric energy. Alternatively, the energy consuming part may be adapted to directly transform the wirelessly transmitted energy into kinetic energy.

It is further preferable to provide a feedback subsystem adapted to wirelessly send feedback information relating to the energy to be stored in the aforementioned energy storage means from inside the human body to the outside thereof. The feedback information is used by the breast implant system to adjust the amount of wireless energy transmitted by the energy transmitter from outside the patient's body. The feedback information provided by the feedback system may be related to an energy balance which is defined as the balance between an amount of wireless energy received inside the human body and an amount of energy consumed by the at least one energy consuming part. Alternatively, the feedback information may relate to an energy balance which is defined as the balance between a rate of wireless energy received inside the human body and a rate of energy consumed by the at least one energy consuming part.

It is further preferred to provide the breast implant system with a control unit to directly or indirectly control one or more elements of the breast implant system. For instance, the control unit may be primarily adapted to control the exchange of fluid at least between the first and second fluid chambers. Preferably, such controlling action is carried out non-invasively from outside the patient's body, such as by wireless remote control. In this case, a part of the control unit is implanted in the patient's body whereas another part is not implanted. In particular in the case where the control unit is completely implanted in the patient's body, a manually operable switch for activating the control unit may be arranged subcutaneously so as to be operable from outside the patient's body.

Where one part of the control unit is provided outside the patient's body and the other part is implanted in the patient's body, the external part of the control unit may be used to program the implanted part of the control unit, preferably wirelessly. Also, the implantable part of the control unit may be adapted to transmit a feedback signal to the external part of the control unit.

The breast implant system of the present invention may be implanted in the patient's body by open surgery or laparoscopic surgery. Open surgery would include the following implantation steps:
    cutting an opening in the skin in the breast area,
    dissecting the area,
    placing at least a part of the adjustable breast implant system in the dissected area, and
    suturing the skin.

A laparoscopic method of implantation would include the following steps:
    inserting a needle like tube into the breast area of the patient's body,
    using the needle like tube to fill the breast area with gas thereby expanding a cavity,
    advancing at least two laparoscopic trocars in the patient's body,
    inserting a camera through one of the trocars,
    inserting at least one dissecting tool through another one of the trocars and dissecting an area of at least one portion of the patient's breast area, and
    placing at least a part of the adjustable breast implant system in the dissected area.

As mentioned in the outset, no part of the breast implant system should penetrate the skin when the skin is sutured.

The invention will now be described in more detail in context with some preferred embodiments of the invention as shown in the accompanying drawings.

BRIEF DESCRIPTION OF THE DRAWINGS

FIGS. 1A to 1C show a breast implant system according to a first embodiment of the present invention, FIG. 11 shows a breast implant system according to an eleventh embodiment of the present invention, FIGS. 12A to 12B show a breast implant system according to a twelfth embodiment of the present invention, and FIGS. 13A to 13B show a breast implant system according to a thirteenth embodiment of the present invention.

FIG. 1A shows very schematically a vertical cross-sectional view of a breast implant system according to a first embodiment. The breast implant system comprises a first fluid chamber 1 and a second fluid chamber 2, each forming part of the breast implant 10 to be implanted in the breast area of a patient. The first and second fluid chambers 1, 2 are fixedly mounted to a rigid back plate 3 with a contour adapted to be placed adjacent the patient's thorax. A fluid line 4 connects the first and second fluid chambers 1, 2 and runs, in the embodiment shown, through the rigid back plate 3. A pump 5 is included in the fluid line 4 and is shown only very schematically. The pump 5 can have many different forms and can be of any suitable type. Also, the actual manner of driving the pump, such as manually or automatically by means of a motor, is of no particular importance and can be chosen appropriately. In the embodiment shown, the pump 5 includes a movable piston in a third fluid chamber 7, the one end of which is connected via the fluid line 4 to the first fluid chamber 1 and the other end of which is connected via the fluid line 4 to the second fluid chamber 2. Using the pump 5, fluid can be pumped and, thus, "exchanged" between the first and second fluid chambers 1 and 2.

In FIG. 1A the fluid chamber 1 is filled with fluid almost to its maximum capacity, so that the overall breast implant 10 is relatively sturdy. FIG. 1B shows the same breast implant 10 with some fluid being removed from the first fluid chamber 1 to the second fluid chamber 2 using the pump 5 (not shown in FIG. 1B). In this state the breast implant 10 is relatively flaccid. FIG. 1C shows the same breast implant with the second fluid chamber 2 being filled almost to its maximum. The volume of the fluid chamber 1 is accordingly decreased. In this case, again, the breast implant 10 is relatively sturdy and is lifted more above the rigid back plate 3 as compared to the state shown in FIG. 1A. The sturdiness of the breast implant 10 in the state shown in FIG. 1C results partly from the fact that a pressure will build up in the second fluid chamber 2 as the volume of the second fluid chamber 2 reaches its maximum capacity.

FIG. 2A shows a simplified structure of a cross-sectional view through a breast implant according to a second embodiment. Unlike FIG. 1, FIG. 2A shows a cross section taken horizontally through the breast implant. A rigid back plate is not provided in this embodiment, but can be provided if desired. The breast implant 10 comprises one first fluid chamber 1 and two second fluid chambers 2. More fluid chambers 1 and more or fewer fluid chambers 2 can also be present. In this embodiment, the fluid chambers 1 and 2 are separated by separating walls 8 made from a polymer material. The separating walls 8 are flexible, but preferably non-stretchable. The outer wall 9 of the fluid chambers 1, 2 is also flexible and preferably stretchable. Valves 11 are provided in the separating walls 8 to allow fluid to be exchanged between the fluid chambers 1, 2. These valves 11 are designed as pressure relief valves and can be of many different types. The purpose of the valves 11 is to allow fluid to flow from one fluid chamber to the next fluid chamber when a predetermined pressure difference is exceeded. In order to allow fluid to flow through the same valve in both directions, the valves 11 are formed as two-way pressure relief valves. A very simple way of providing such two-way pressure relief valve is shown in FIG. 2C. Accordingly, there is a slit 12 in the flexible separating wall 8 which opens when a certain pressure difference between the adjacent fluid chambers is exceeded. FIG. 2A shows a "medium" state of the breast implant 10. However, FIG. 2A also shows by dotted lines one possible extreme state of the breast implant 10. That is, when the pressure in the second fluid chambers 2 is increased, such as by the patient manually compressing the second fluid chambers 2, fluid will flow into the first fluid chamber 1, as shown by the arrows. Then, when the patient releases the pressure on the second fluid chambers 2, the breast implant 10 will assume the shape as shown by the dotted lines.

FIG. 2B shows another extreme state of the breast implant 10 of FIG. 2A. In this case, when the pressure in the first fluid chamber 1 is increased, fluid is made to flow into the adjacent second fluid chambers 2, as indicated in FIG. 2B by the arrows. Once the pressure is released, the breast implant 10 will take the shape as shown in FIG. 2B by the dotted lines. Accordingly, the patient can easily change the shape of the breast implant 10 between the three states shown in FIGS. 2A and 2B. Additional intermediate states can also be achieved and even other forms can be achieved, for instance when only one of the two second fluid chambers 2 is compressed to urge fluid into the neighboring first fluid chamber 1.

FIGS. 3A and 3B show the breast implant 10 of FIGS. 2A, 2B covered on the outside with a layer 13 of soft material according to a third embodiment. The layer 13 may be formed by a liquid or gel type silicone or by a foam or a combination thereof. Also, bubbles of air or collagen may be incorporated in the silicone, foam or other soft material. The compartment forming the layer 13 is completely separate from the interconnected first and second chambers 1, 2. Again, a rigid back plate 3 is provided in this embodiment, but can be dispensed with if desired. FIGS. 3A and 3B demonstrate how such outer layer 13 can level out irregularities of the fluid chamber walls. More importantly, however, the outer layer 13 forms a barrier between the flexible, stretchable inner fluid chambers 1, 2 and any fibrosis that might form on the outside of the breast implant.

FIGS. 4A and 4B show a fourth embodiment of a breast implant. Again, a rigid back plate 3 is provided to which a first fluid chamber 1 and a second fluid chamber 2 are fixedly mounted. By means of the pump 5 which—in the embodiment shown—is again integrated in the rigid back plate 3, fluid can be exchanged between the first and second fluid chambers 1, 2. The first fluid chamber 1 together with the back plate 3 defines an enclosed space forming a third fluid chamber 14. The third fluid chamber 14 comprises a compressible medium, such as a gas or a foam in which the gas is contained. Fluid is exchanged only between the first and second chambers 1, 2, whereas the third fluid chamber 14 is completely isolated, being separated from the first fluid chamber by separating wall 15 and from the second fluid chamber 2 by separating wall 16. Both separating walls 15, 16 are flexible and at least the separating wall 15 should be non-stretchable.

Figure 3A:
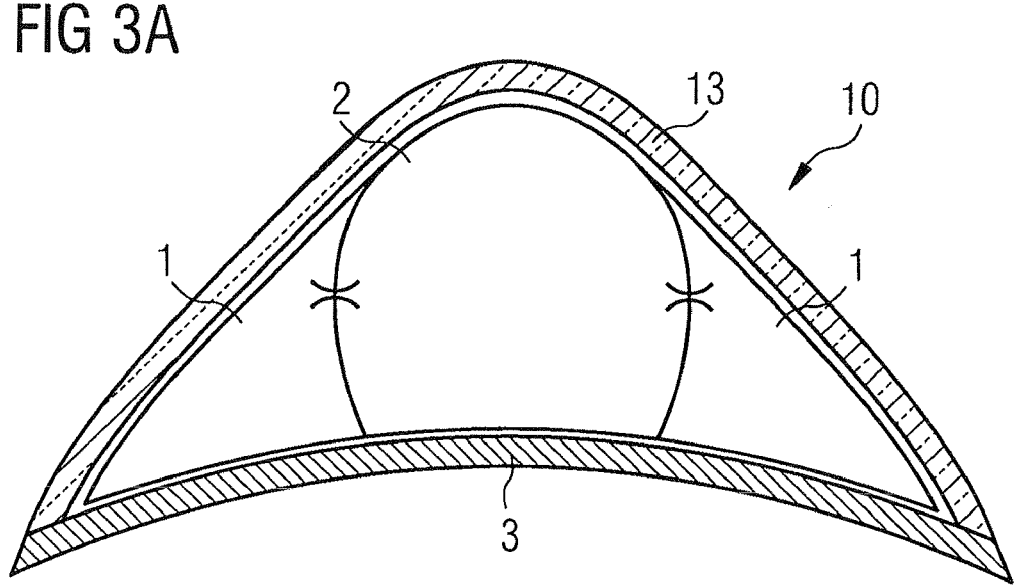
FIGS. 3A to 3B show a breast implant system according to a third embodiment of the present invention.
Figure 3B:
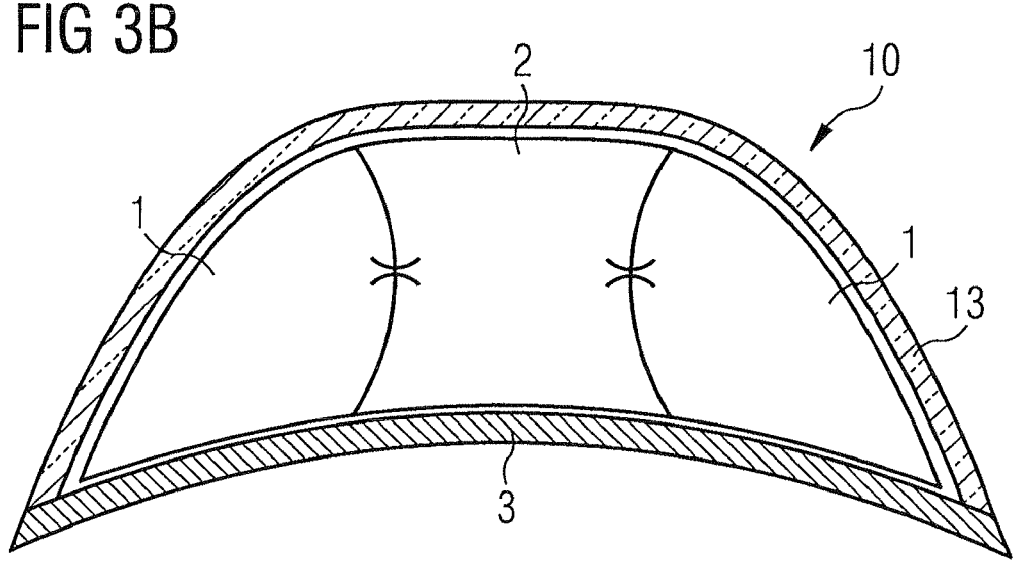
Figure 4A:
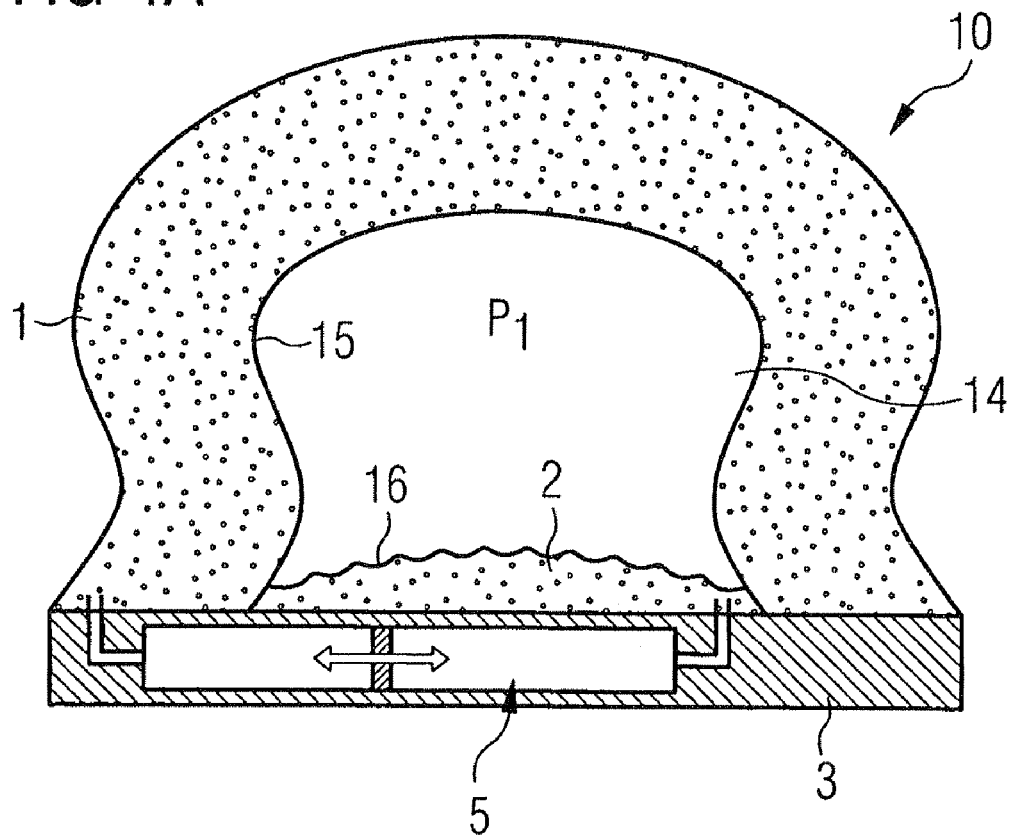
FIGS. 4A to 4B show a breast implant system according to a fourth embodiment of the present invention.
Figure 4B:
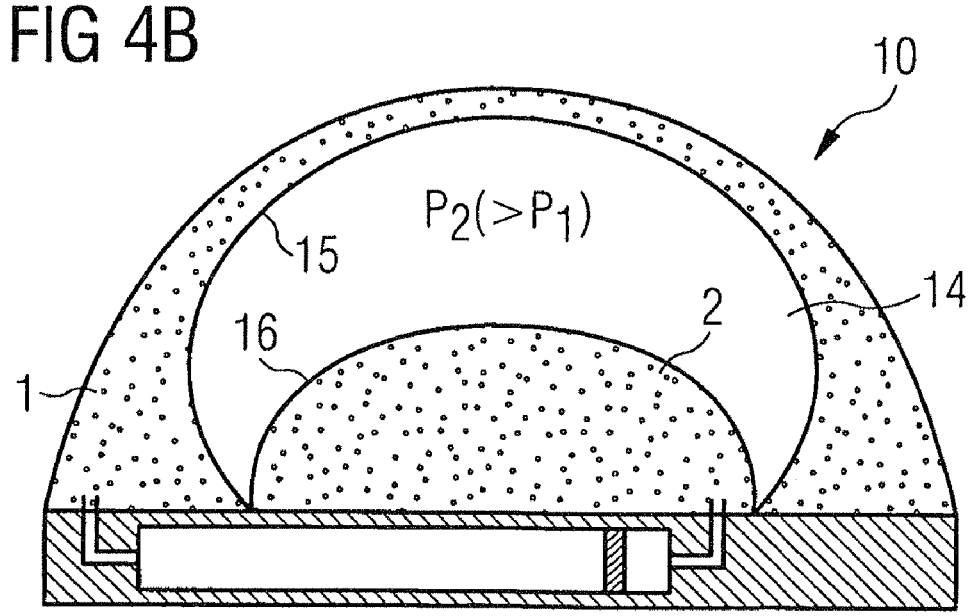

When fluid is pumped from the first fluid chamber 1 into the second fluid chamber 2, the volumes of the fluid chambers 1 and 2 will change accordingly, as is shown in FIG. 4B. The outer wall of the first fluid chamber 1 is elastic—in the embodiment shown—so as to adapt to the reduced volume, but may also be non-elastic, provided that it is sufficiently flexible to conform to the changed volume. Again, an outer layer 13, as shown in FIGS. 3A, 3B, can be provided here (and in all embodiments described herein). Due to the fact that the separating wall 15 is non-stretchable, the increased volume of the second fluid chamber 2 causes the pressure in the third fluid chamber 14 to rise from an initial pressure P1 to a raised pressure P2. Altogether, not only has the shape of the breast implant 10 dramatically changed, but the volume has also changed. However, the mass and, thus, the weight of the breast implant has not changed at all.

Figure 5A:
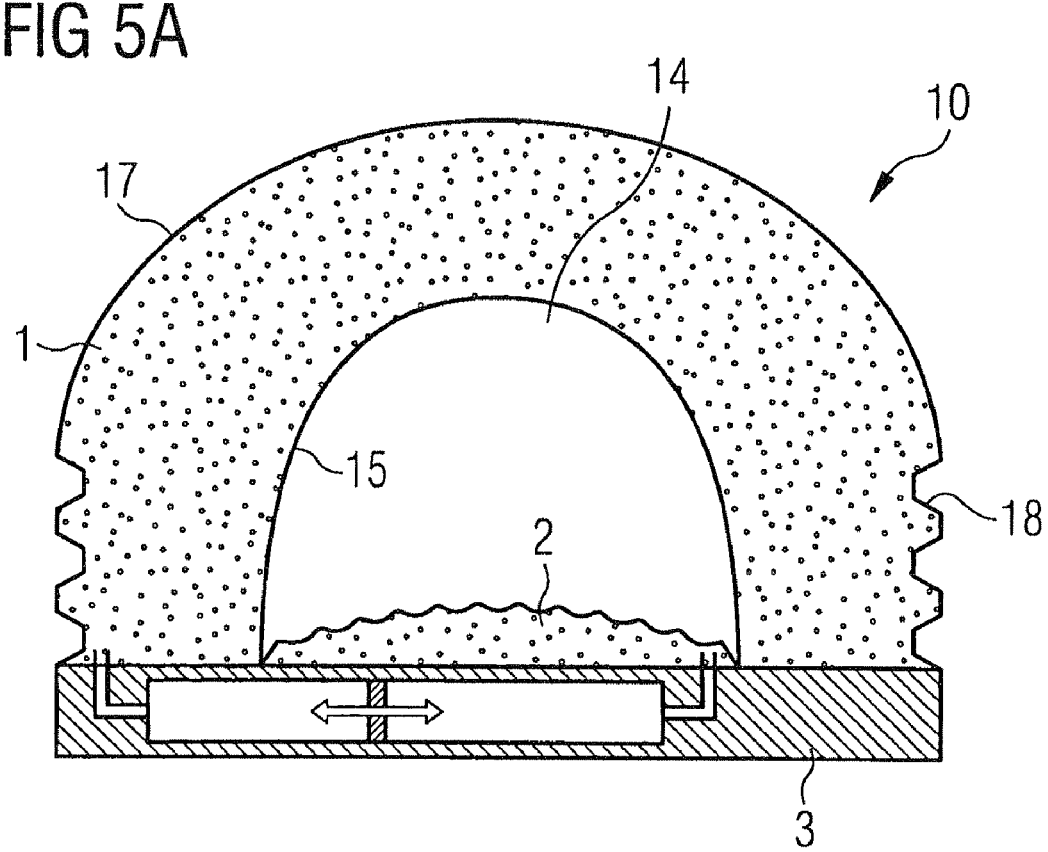
FIGS. 5A to 5B show a breast implant system according to a fifth embodiment of the present invention.
Figure 5B:
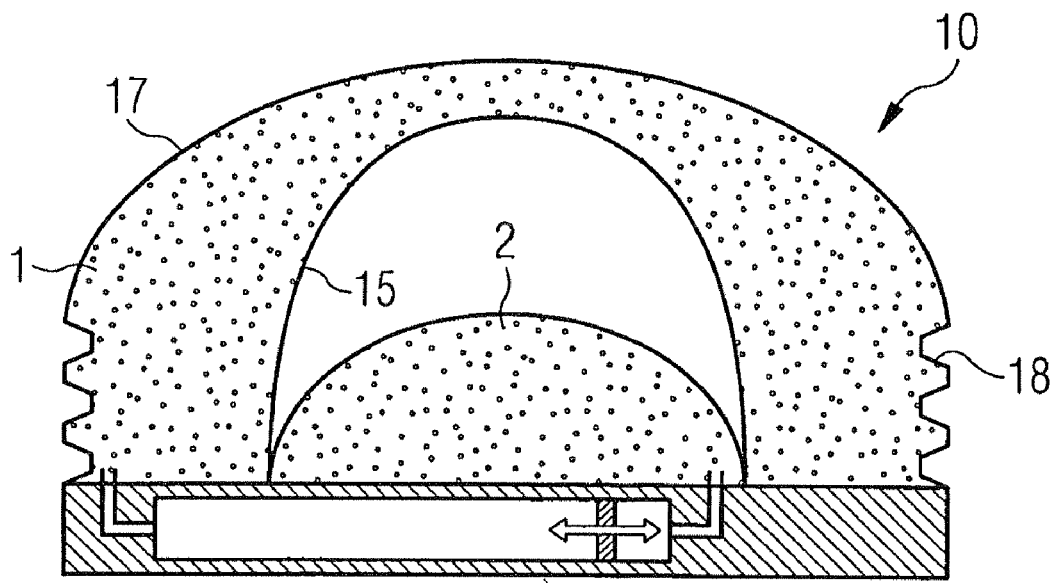

In the embodiment shown in FIGS. 4A, 4B, the elastic, non-stretchable wall 15 surrounding the third fluid chamber 14 may be replaced with a rigid wall of constant form. A fifth embodiment similar to the one shown in FIGS. 4A, 4B, but with a rigid separating wall 15, is shown in FIGS. 5A, 5B. The outer wall 17 of the first fluid chamber 1, which in this particular embodiment constitutes the outermost wall of the breast implant 10, comprises pleat-like folds 18. The pleat-like folds are trapezoidal in cross section in order to allow the folds 18 to be expanded and compressed irrespective of any fibrosis that has formed on the outer surface 17. Thus, due to these folds 18, fibrosis forming on the breast implant 10 will not hinder the enlargement of the breast implant 10.

It should be understood that the membrane 16 separating the incompressible fluid in the second chamber 2 from the compressible fluid, such as gas, in the third chamber 14 can be dispensed with in cases where there is no danger of compressible fluid from the gas chamber 14 reaching the first chamber 1. For instance, if the patient is lying down when the incompressible fluid is being re-transferred from the gas chamber 14 to the first fluid chamber 1, this would be a safe way to prevent any gas from being transferred from the gas chamber 14 to the fluid chamber 1.

Figure 2A:
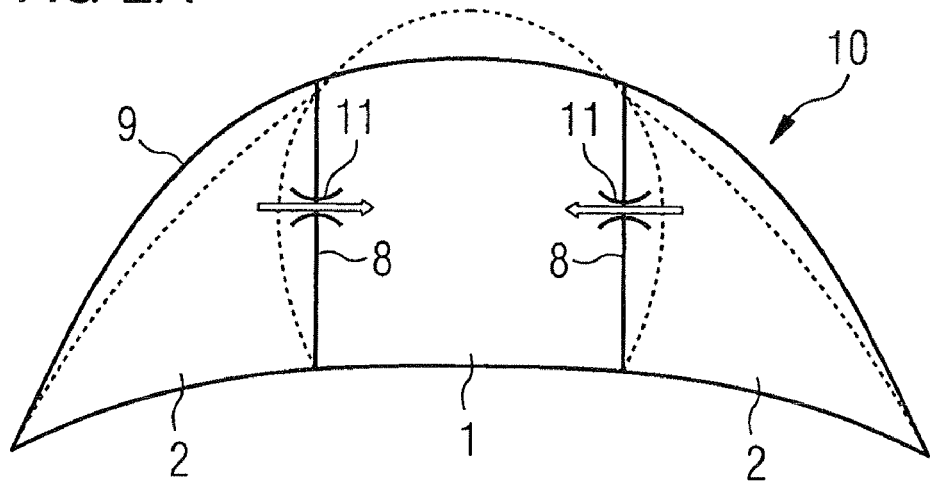
FIGS. 2A to 2C show a breast implant system according to a second embodiment of the present invention.
Figure 2B:
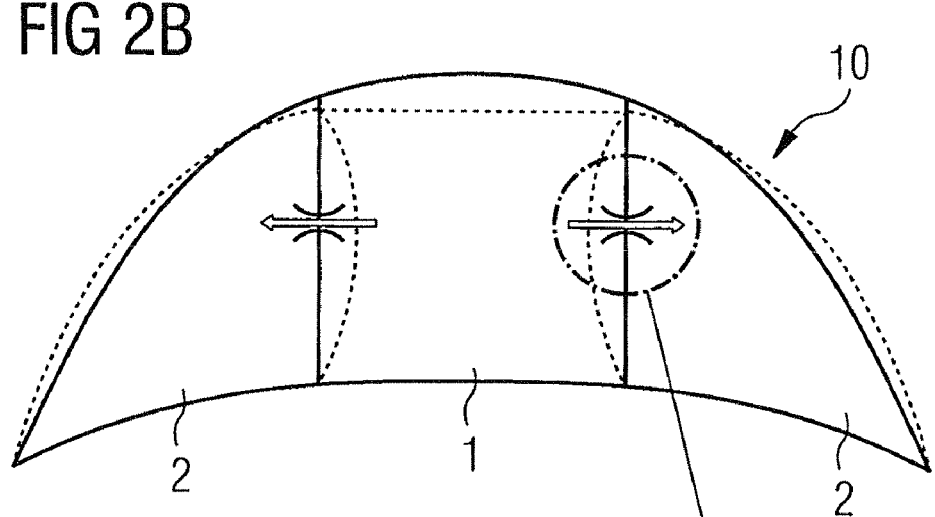
Figure 2C:
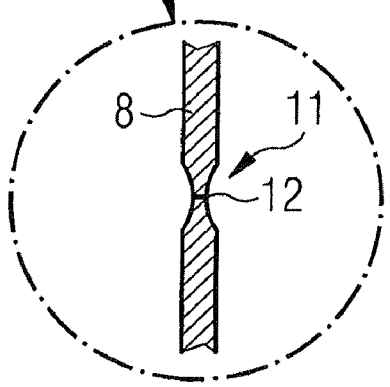
Figure 6A:
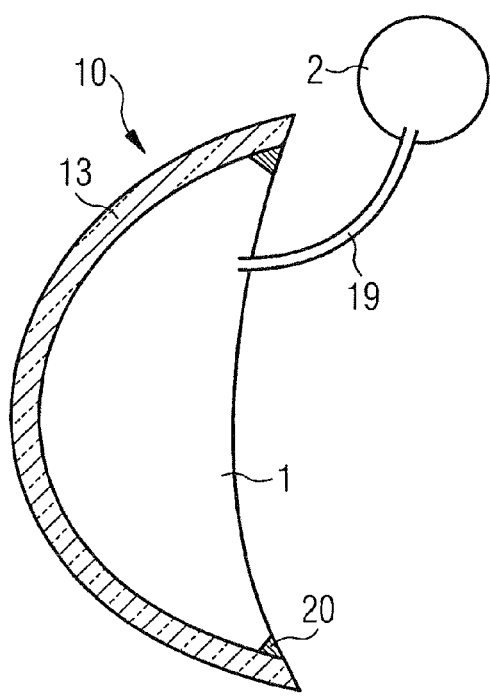
FIGS. 6A to 6B show a breast implant system according to a sixth embodiment of the present invention.
Figure 6B:
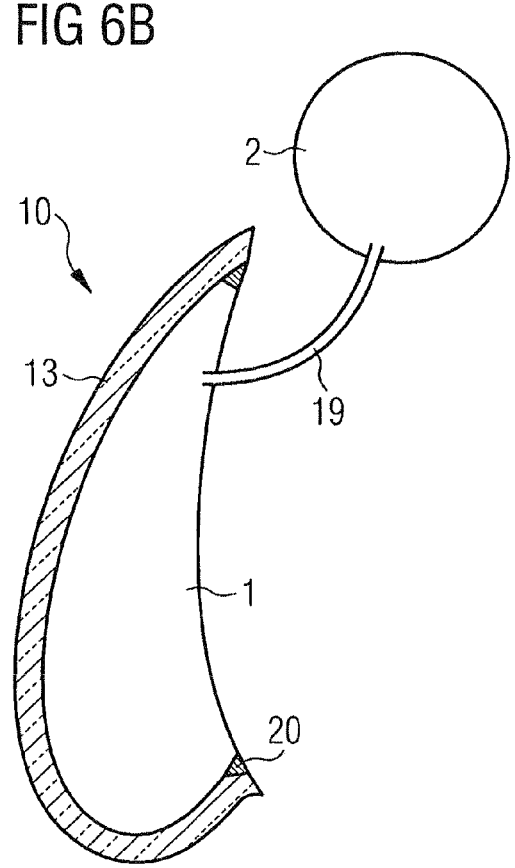

While FIGS. 1 to 3 relate to breast implants with constant volume and weight but variable shape, and FIGS. 4 and 5 relate to embodiments with a constant weight but variable shape and volume, the following embodiments relate to breast implants where the variable shape and volume involves a weight change of the breast implant. More specifically, at least one of the second fluid chambers 2 is implanted in the patient's body remote from the breast implant 10 and is connected to the first fluid chamber or chambers 1 in the breast implant 10 via one or more fluid lines 19. An example is shown in FIGS. 6A and 6B. FIGS. 6A and 6B show as a sixth embodiment a cross-sectional view through the breast implant 10 similar to the cross-sectional view in FIG. 1. In the specific embodiment shown, an outer layer 13 similar to the outer layer 13 in FIG. 3 is provided as an option. An angular frame 20 to be placed close to the patient's thorax provides stability to the breast implant 10. The first fluid chamber 1 is fixedly connected to such frame 20. By removing fluid from the first fluid chamber 1 in the breast implant 10 into the remotely implanted second fluid chamber 2, one can change the look and feel of the breast implant 10 from sturdy to flaccid, as can be seen in FIGS. 6A and 6B.

FIGS. 6A and 6B only show the principle of the system. Not shown is the exact location of the second fluid chamber 2 in the patient's body, nor the specific way of exchanging the fluid between the first and second fluid chambers 1, 2. As to the location of implantation in the patient's body, the second fluid chamber 2 may be implanted in the patient's abdominal cavity or in the patient's chest area. More specifically, it may be placed outside the patient's thorax, in particular under the pectoralis muscle. The latter location can be easily reached during the surgery when the breast implant 10 is implanted, and this location does not disturb the patient very much.

Alternatively, the second fluid chamber 2 may be arranged subcutaneously so that it is easily accessible from the outside of the patient's body. The patient can then compress the second fluid chamber 2 in order to urge fluid into the first fluid chamber 1 of the breast implant 10, whereas the return flow into the remotely implanted second fluid chamber 2 can be achieved, e.g. by manually compressing the breast implant 10. Many variants of regulating the fluid flow between the first and second fluid chambers 1, 2 are conceivable, and one of those options will be described in the following with respect to another embodiment.

Figure 7A:
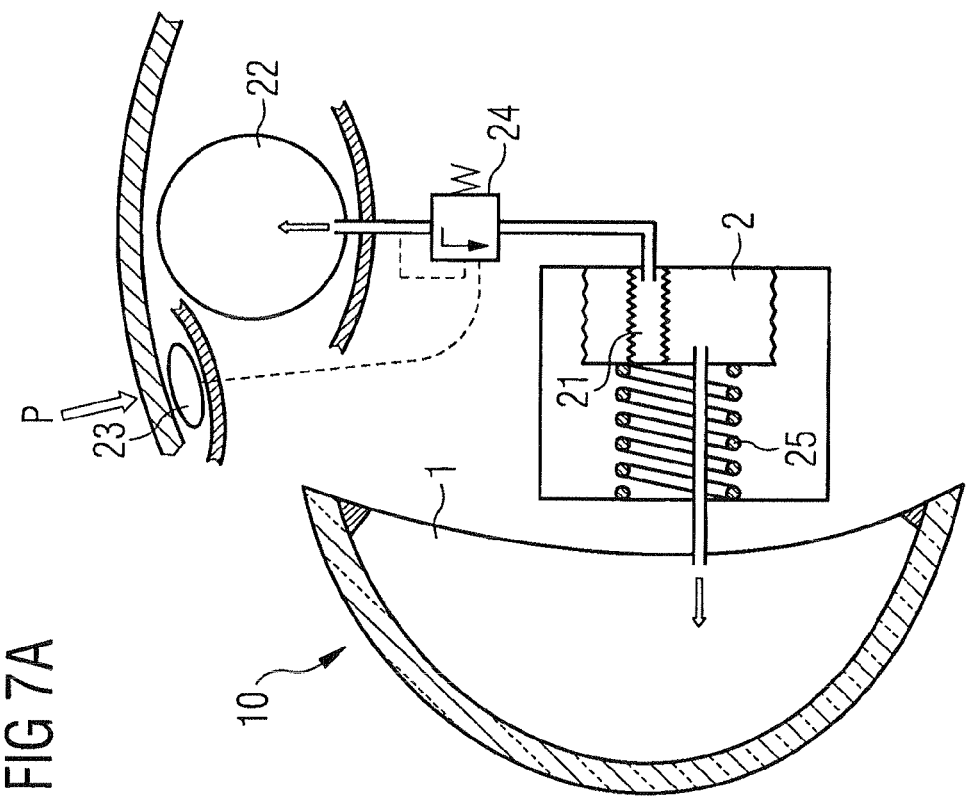
FIGS. 7A to 7B show a breast implant system according to a seventh embodiment of the present invention.
Figure 7B:
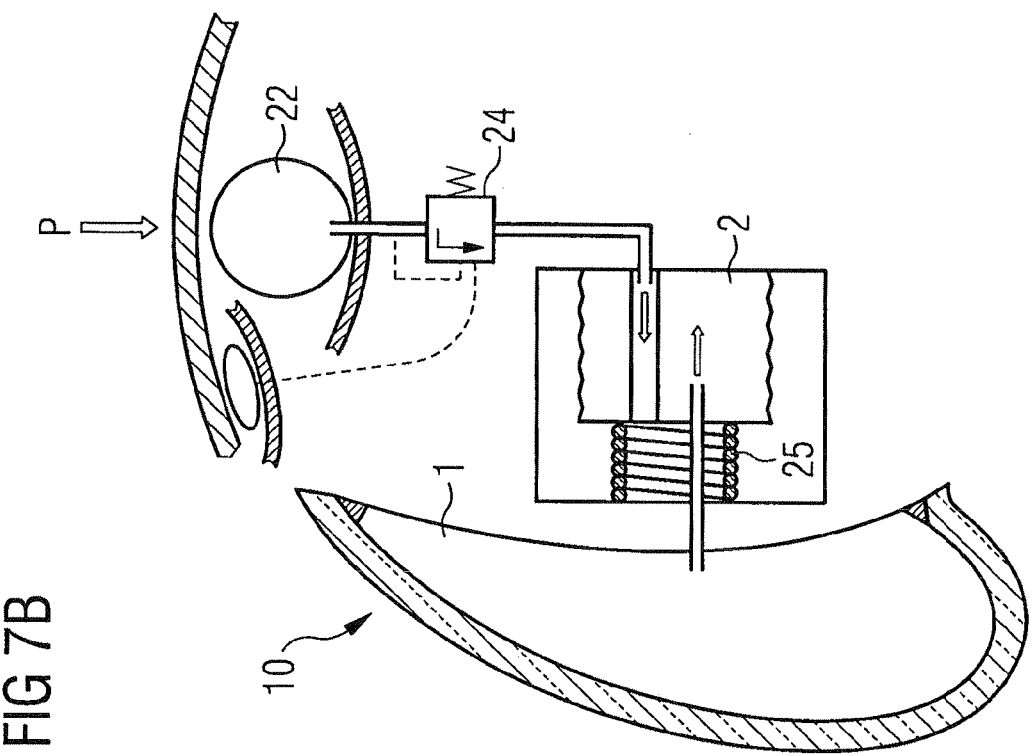

FIGS. 7A and 7B show a seventh embodiment of a breast implant system including a servo system. Apart from the servo system, one variant of regulating the fluid flow between the first and second fluid chambers 1, 2 by means of a subcutaneously implanted fluid chamber will also be described in the context of this embodiment.

More specifically, the second fluid chamber 2, which is interconnected with the first fluid chamber 1 in the breast implant 10 and implanted in the patient's body remote from the breast implant 10, has the form of a bellows. Operatively connected to the bellows 2 is a third fluid chamber comprising two sub-chambers 21 and 22. The sub-chamber 21 cooperates with the bellows 2 such that filling of the sub-chamber 21 with a fluid from the sub-chamber 22 will cause the bellows 2 to extend. The situation is such, however, that the volume change in the sub-chamber 21, which is also in the form of a bellows, is less than the volume change in the bellows 2. In turn, when fluid is removed from the sub-chamber 21 into the sub-chamber 22, the length and, thus, the volume of the second fluid chamber 2 decreases.

The way of obtaining a sturdy breast implant is shown in FIG. 7A. That is, when the patient has a subcutaneously arranged pressure chamber 23 in order to open a valve 24 to allow fluid to flow between sub-chambers 21 and 22, a preloaded spring 25 will cause the second fluid chamber 2 to decrease, thereby urging not only fluid from the sub-chamber 21 to flow to the sub-chamber 22 but also fluid from the second fluid chamber 2 to flow into the first fluid chamber 1 of the breast implant 10. The breast implant 10 will balloon accordingly. When pleased with the amount of ballooning of the breast implant, the patient will simply stop pressing the pressure chamber 23, so that the valve 24 closes.

When desiring to put the breast implant 10 back into a flaccid state, the patient can simply compress the subcutaneously implanted sub-chamber 22. This is shown in FIG. 7B. The increased pressure in the sub-chamber 22 will cause the valve 24, which is designed as a pressure relief valve, to open so that fluid flows from the sub-chamber 22 into the sub-chamber 21. The sub-chamber 21 will expand accordingly against the force of the spring 25. This will in turn cause the second fluid chamber 2 to expand also, and fluid will be drawn from the fluid chamber 1 of the breast implant 10 into the remotely implanted fluid chamber 2 of the servo system.

With the servo system shown in FIGS. 7A and 7B, the subcutaneously implanted sub-chamber 22 can be kept relatively small so that it will not disturb the patient's appearance too much. As a negative side effect, the pressure that the patient has to apply to the sub-chamber 22 in order to overcome the force of the spring 25 is relatively high. However, if the spring load is kept small, this has the effect that the inflation of the first fluid chamber 1 in the breast implant 10 by automatic action of the spring 25 takes somewhat longer.

Figure 8A:
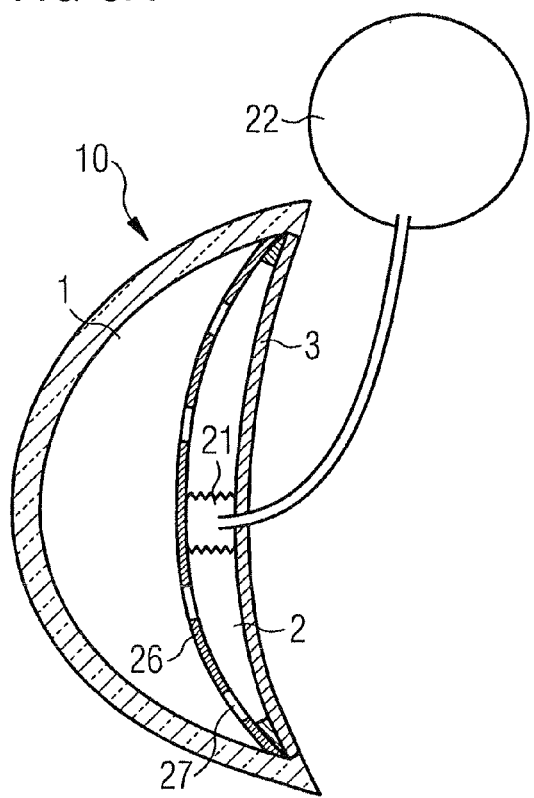
FIGS. 8A to 8B show a breast implant system according to an eighth embodiment of the present invention.
Figure 8B:
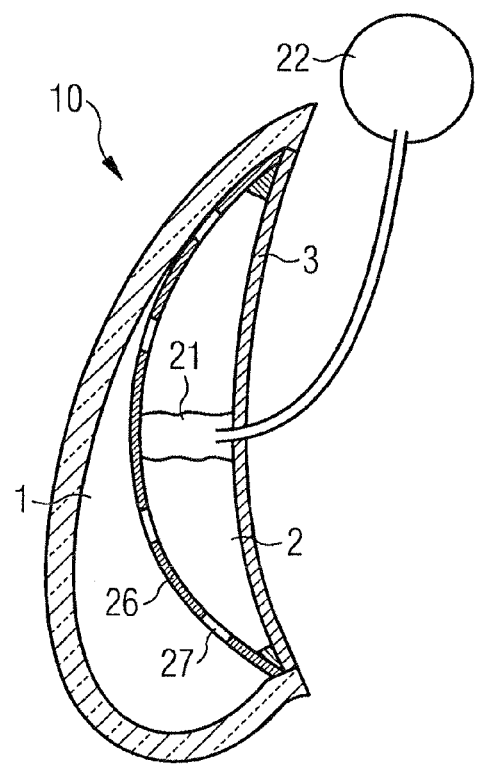

FIGS. 8A and 8B show a different servo system. The difference here is that the second fluid chamber 2 is not remotely implanted but forms part of the breast implant 10. The breast implant 10 comprises a rigid back plate 3 and a relatively stiff, but nevertheless flexible separating wall 26 separating the first and second fluid chambers. The separating wall 26 has openings 27 to allow fluid to be exchanged between the first and second fluid chambers 1, 2. The separating wall 26 is fixedly connected to the rigid back plate 3, with its normal position shown in FIG. 8A.

In the servo system shown in FIGS. 8A and 8B the sub-chamber 21 is again in the form of a bellows which extends between the rigid back plate 3 and the relatively stiff but nevertheless elastic separating wall 26. When the sub-chamber 21 is filled with fluid from the sub-chamber 22, the sub-chamber 21 will expand lengthwise, thereby urging apart the relatively stiff separating wall 26 and the rigid back plate 3. This in turn will cause fluid to flow from the first fluid chamber 1 through the separating wall 26 into the second fluid chamber 2. As a result, the shape of the breast implant 10 changes, which change is shown in FIG. 8B somewhat exaggerated. Again, the manner of controlling fluid to flow between the two sub-chambers 21 and 22 may be user-defined and realized e.g. in the same manner as described in relation to FIGS. 7A and 7B. The spring force required to compress the sub-chamber 21 in order to generate a return flow from the second fluid chamber 2 into the first fluid chamber 1 is provided by the elasticity of the relatively stiff separating wall 26, due to the fact that it is fixedly connected to the rigid back plate 3, similar to the functioning of a bow (of a bow and arrow).

Figure 9A:
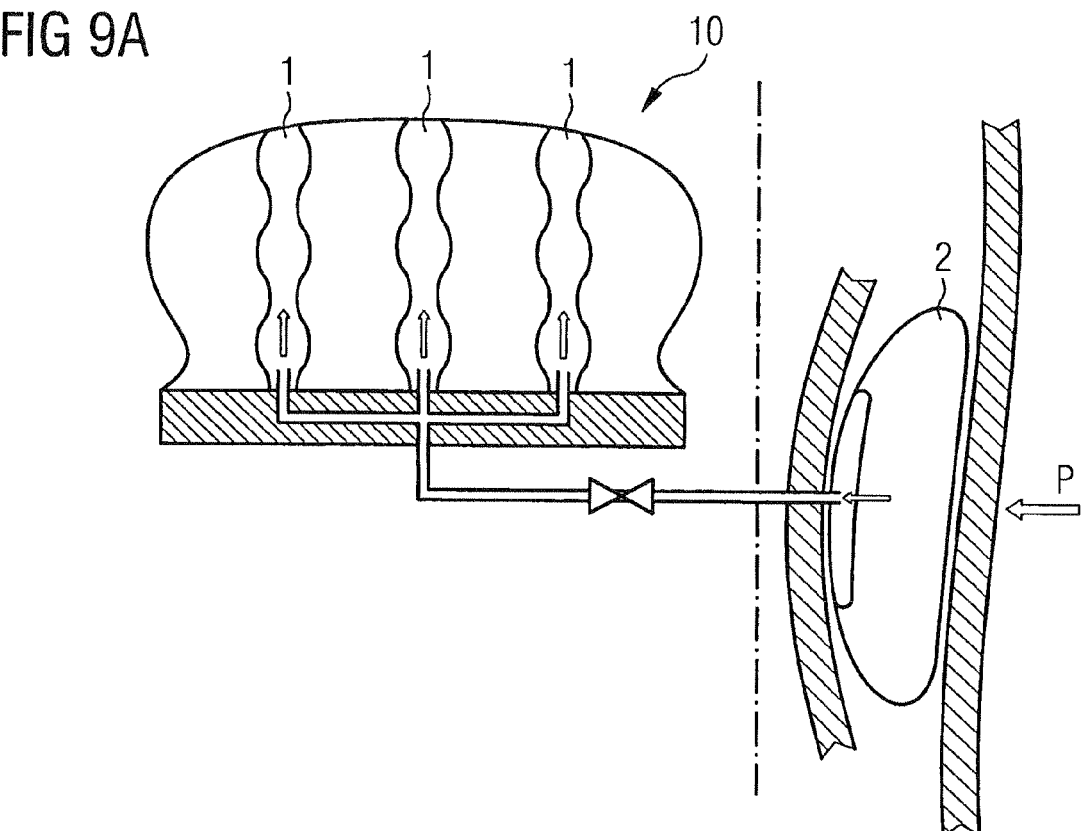
FIGS. 9A to 9C show a breast implant system according to a ninth embodiment of the present invention.
Figure 9B:
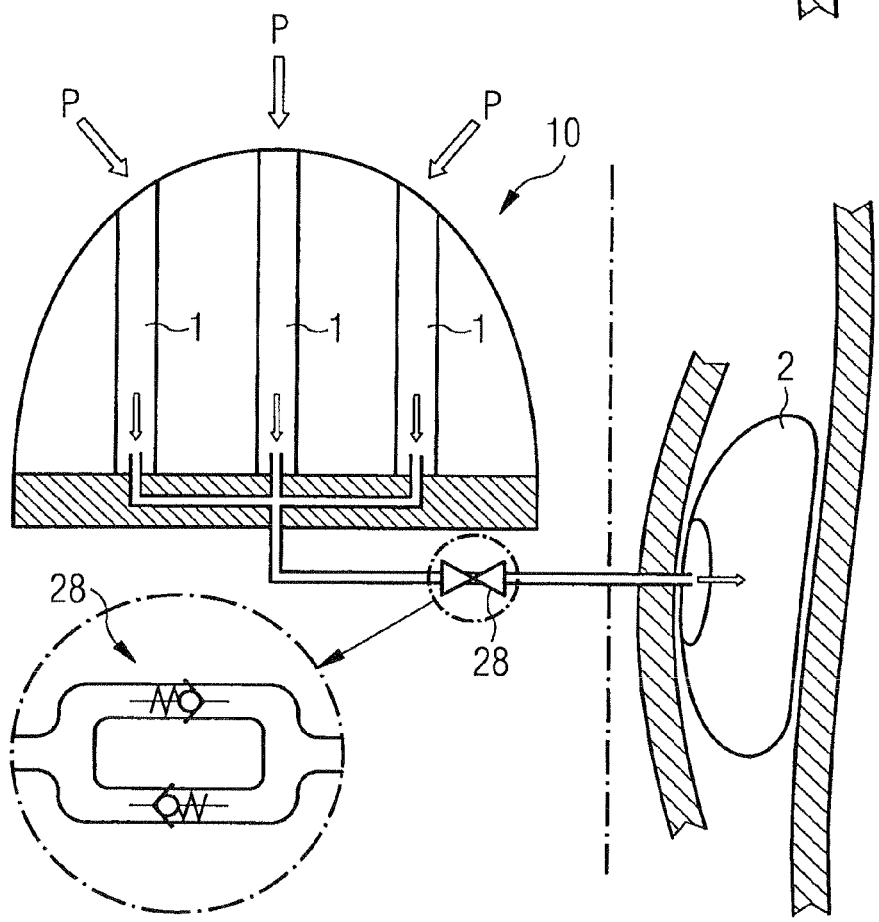

FIGS. 9A to 9B show a ninth embodiment with a plurality of first chambers 1 in the breast implant 10. The first chambers 1 only fill a part of the breast implant 10, whereas the major part of the breast implant is filled with a different material, such as a foam or a silicone or a combination thereof. Artificially produced collagen can also be used to fill the breast implant 10. The second fluid chamber 2 is again implanted subcutaneously here. As becomes clear from FIG. 9A, a little amount of fluid transferred from the second fluid chamber 2 into the first fluid chambers 1 of the breast implant will cause a substantial change of the breast implant's shape. FIG. 9B shows the shape of the breast implant 10 with fully inflated first fluid chambers 1. By manual compression of the breast implant 10, as indicated by arrows P in FIG. 9B, the fluid in the first fluid chambers 1 of the breast implant 10 can be urged back into the remotely implanted second fluid chamber 2, in order to regain the flaccid state shown in FIG. 9A.

Figure 9C:
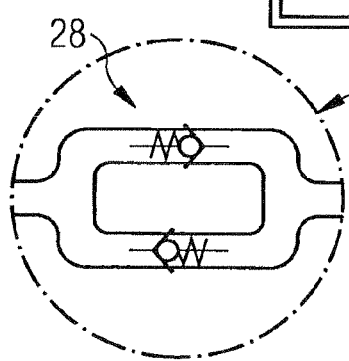

A two-way non-return valve 28 may be placed in the line 29 connecting the first and second fluid chambers 1, 2. The two-way non-return valve 28 is schematically shown in more detail in FIG. 9C.

Figure 10:
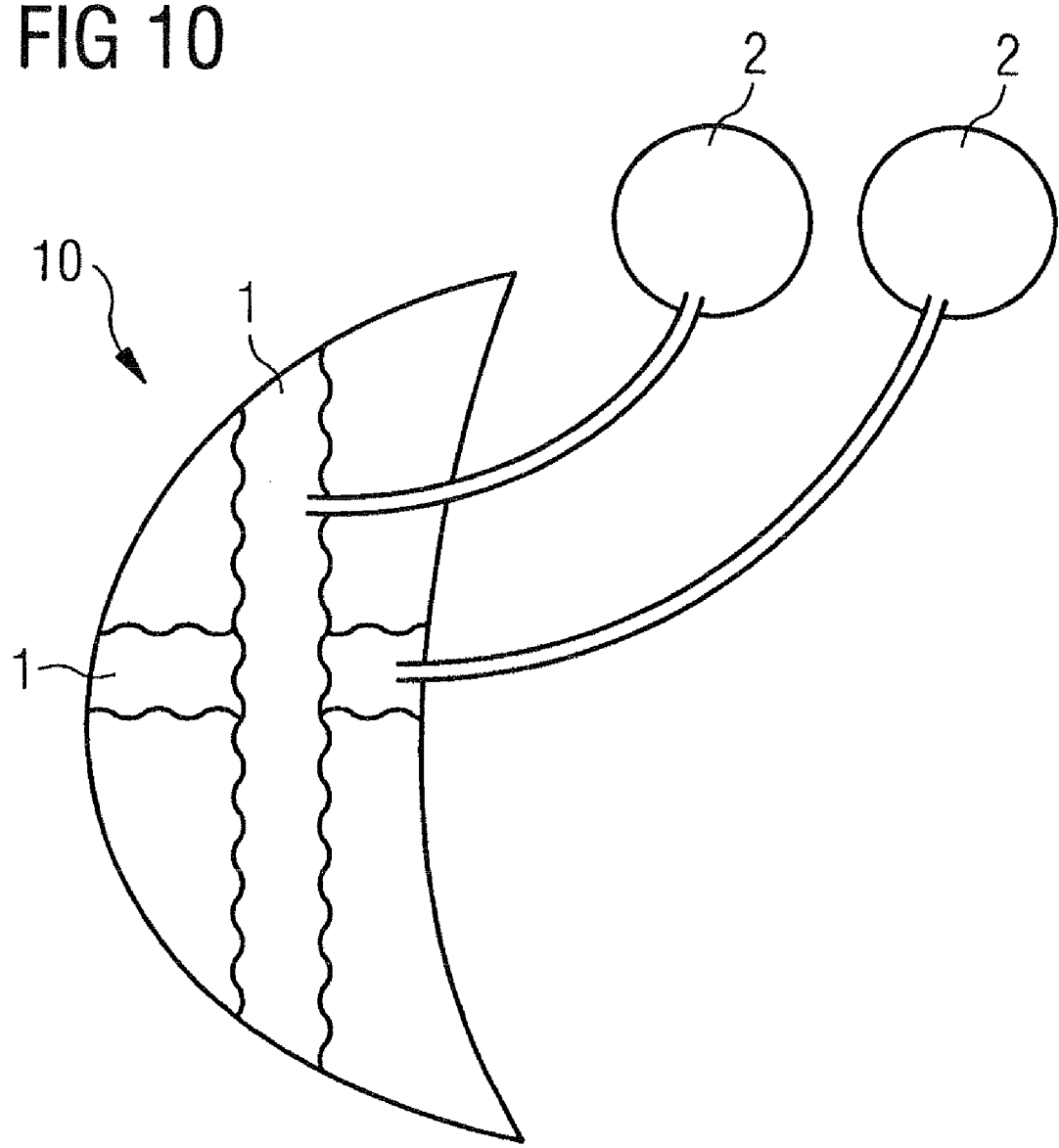
FIG. 10 shows a breast implant system according to a tenth embodiment of the present invention.

FIG. 10 shows a tenth embodiment to demonstrate that the breast implant 10 may comprise a plurality of first fluid chambers 1 in an arbitrary arrangement, and a plurality of second fluid chambers 2 in fluid connection with the first fluid chambers 1 may be provided remote from the breast implant 10. In particular, the second fluid chambers 2 may be implanted subcutaneously for direct manual use by the patient. A second fluid chamber 2 may be connected to one or more of the first fluid chambers 1. Likewise, a first fluid chamber 1 may be connected to one or more of the second fluid chambers 2. This permits the design of a breast implant 10 according to very personal needs.

FIG. 11 shows a more complex breast implant system. The basic structure of the breast implant system corresponds to the structure described above in relation to FIGS. 9A and 9B, but could also be completely different. What is important in the eleventh embodiment of FIG. 11 is a pump P driven by a motor M and arranged to pump fluid between the first and second fluid chambers 1, 2. The fluid chamber 2 may be implanted anywhere in the patient's body, such as in the abdominal cavity.

The motor M is energized with wirelessly transmitted energy. For this purpose, the breast implant system comprises an energy transmitter 29 outside the patient's body and an energy transforming device 30 inside the patient's body, preferably subcutaneously implanted, to transform the wireless energy into electric energy. While it is possible to make use of a motor M adapted to directly transform the wirelessly transmitted energy into kinetic energy, or, alternatively, to use the wirelessly transmitted energy transformed into electric energy by means of the energy transforming device 30 to drive the motor M as the energy transforming device transforms the wireless energy into the electric energy, the specific embodiment shown in FIG. 11 first stores the transformed electric energy in an energy storage means E, before it is supplied to the motor M. Of course, it is also possible that a part of the transformed electric energy is directly used by the motor while another part of the transformed electric energy is stored in the energy storage means E. The energy storage means E may include an accumulator such as a rechargeable battery and/or a capacitor. It is less convenient, but possible, to implant a regular battery as the energy storage means E. But a regular battery may be used as the energy source to provide the wireless energy to be transmitted from outside the patient's body.

The breast implant system shown in the specific embodiment of FIG. 11 further includes a control unit. The control unit here comprises a first part C1 to be used by the patient from outside the patient's body and a second part C2 to be implanted inside the patient's body. Data can thus be transmitted wirelessly between the first and second parts C1, C2 of the control unit. In addition or alternatively, the implantable second part C2 of the control unit may be programmable via the first part of the control unit. Preferably, the data are transmitted between the first and second parts C1, C2 of the control unit in the same manner as energy is transmitted, such as via the elements 29 and 30.

The external part C1 of the control unit may also be replaced with a simple manually operable switch for activating the implantable control unit C2. Such switch is then arranged for subcutaneous implantation so as to be operable from outside the patient's body. It is also possible to combine the switch with an external part C1 of the control unit.

Furthermore, feedback information may be sent between the implanted part C2 and the external part C1 of the control unit. Such feedback information may include information related to the energy to be stored in the energy storage means E. The control unit can make use of such feedback information for adjusting the amount of wireless energy transmitted by the energy transmitter 29. The feedback information may be related to an energy balance, which may be defined either as the balance between an amount of wireless energy received inside the human body and an amount of energy consumed by the motor and pump, or as the balance between a rate of wireless energy received inside the human body and a rate of energy consumed by the motor and pump.

FIG. 11 shows an injection port 31 implanted under the patient's skin. Fluid can be added to or removed from the breast implant system by means of a regular syringe if need arises. While only one injection port 31 is shown in FIG. 11, two or more injection ports may be provided in order to allow for individual adjustment of the fluid volume in the particular fluid chambers. The injection port 31 can also be used to equalize a pressure difference between one or more of the fluid chambers.

In context with a twelfth embodiment of a breast implant system, FIGS. 12A and 12B show a manner of implanting the second fluid chamber or chambers remote from the breast implant under the pectoralis muscle. The breast implant 10 is here formed from a single first chamber 1, but can as well comprise more than one first fluid chamber 1. It is designed to increase the volume of a natural breast 50, but can likewise be designed to replace an amputated breast. The second fluid chamber 2 (or fluid chambers) serves as a reservoir for the first fluid chamber and is implanted remote from the first fluid chamber 1 underneath the patient's minor pectoralis muscle 40 next to the patient's thorax. A pump 5 is also implanted remote from the breast implant 10 to exchange fluid between the first and second fluid chambers 1, 2. The pump 5 may be combined with a motor, control unit and other parts of the systems previously described. Instead of or in addition to the pump 5, other elements of the breast implant system embodiments described above may be combined with this twelfth embodiment, such as remotely implanted elements for manual operation by the patient, pressure relief valves and so forth.

In this twelfth embodiment, the second fluid chamber 2 is wide and flat as compared to the first fluid chamber 1, i.e. it has a substantially larger surface-to-volume ratio than the first fluid chamber 1. This allows a substantial subjective volume change of the patient's breast 50 to be achieved by pumping fluid between the first and second fluid chambers 1, 2, as can be seen from a comparison of FIGS. 12A and 12B showing the breast implant system with differently filled first and second fluid chambers 1, 2.

Due to the relative dimensions of the second fluid chamber, the second fluid chamber 2 has merely the function of providing a reservoir for the first fluid chamber 1 and does not itself contribute much to the shape of the patient's breast 50. It is therefore accurate to say that the first fluid chamber 1 forms part of the breast implant 10, whereas the second fluid chamber 2 merely serving as a reservoir is "remotely implanted" and, thus, does not form part of the breast implant 10, even though it is located in the area of the patient's breast above the thorax. Alternatively, where the surface-to-volume ratio of the first and second fluid chambers 1, 2 are in the same order of magnitude, in particular almost identical, a volume change in either of the fluid chambers effectively contributes to a change in the shape of the patient's breast 50, in which case it is accurate to say that both the first and second fluid chambers 1, 2 form part of the breast implant 10.

It is conceivable and can even be preferable to place both the second fluid chamber 2 along with at least one first fluid chamber 1 underneath the patient's minor pectoralis muscle 40 or to place the first fluid chamber 1 between the patient's major and minor pectoralis muscles. In this case the first fluid chamber 1 would still be considered to form part of the breast implant 10 and the second fluid chamber 2 would still be considered implanted remote from the breast implant 10, when due to their substantially different surface-to-volume ratios the second fluid chamber 2 merely functions as a reservoir not substantially contributing to the overall shape of the patient's breast 50 and the first fluid chamber 1 mainly contributes to the shape variations of the patient's breast 50. Alternatively, when both the first and second fluid chambers 1, 2 have substantially the same surface-to-volume ratio, then also volume changes in the second fluid chamber 2 substantially contribute to the changes in the shape of the patient's breast 50 and, therefore, must be considered to form part of the breast implant.

FIGS. 13A and 13B show, in context with a thirteenth embodiment of a breast implant system, a different manner of how the second fluid chamber or chambers can be implanted remote from the breast implant under the pectoralis muscle. This embodiment differs from the one described in relation to FIGS. 12A and 12B in that the second fluid chamber 2 (or fluid chambers) is implanted between the patient's minor pectoralis muscle 40 and major pectoralis muscle 41. Also in this thirteenth embodiment, the second fluid chamber 2 is wide and flat as compared to the first fluid chamber 1, i.e. it has a substantially larger surface-to-volume ratio than the first fluid chamber 1, so that a substantial subjective volume change of the patient's breast 50 can be achieved by pumping fluid between the first and second fluid chambers 1, 2. The arrangement of the second fluid chamber 2 between the major and minor pectoralis muscles can be more convenient for the patient.

Again, it is conceivable and can even be preferable to place both the second fluid chamber 2 along with at least one first fluid chamber 1 between the pectoralis muscles.

The invention claimed is:

1. A breast implant system, comprising:
    a plurality of chambers including:
    at least one first fluid chamber, and
    at least one second fluid chamber,
    said first and second fluid chambers being adapted for implantation in the human body with the at least one first fluid chamber forming part of a breast implant,
    said fluid chambers being interconnected when implanted such that fluid can be exchanged back and forth between the first and second fluid chambers so as to change their respective fluid content without the need to administer or remove any fluid through the patient's skin,
    wherein at least one of said at least one second fluid chamber is adapted for implantation within the human body remote from the breast implant so as to form a reservoir for the at least one first fluid chamber,
    the breast implant system further comprising at least one conduit between the remotely implantable second fluid chamber and the at least one first fluid chamber for fluid exchange between the first and second fluid chambers.

2. The breast implant system of claim 1, wherein the breast implant has a variable volume, the volume being variable upon fluid exchange between the first and second fluid chambers.

3. The breast implant system of claim 1, comprising more than two fluid chambers.

4. The breast implant system of claim 3, wherein two or more of said at least one first fluid chamber form part of the breast implant.

5. The breast implant system of claim 4, comprising a valve adapted to change fluid communication between the at least one second fluid chamber and anyone of the first fluid chambers.

6. A breast implant system, comprising:
    a plurality of chambers including
    at least one first fluid chamber, and
    more than two second fluid chambers,
    said first fluid chamber and said more than two second fluid chambers being adapted for implantation in the human body with the at least one first fluid chamber forming part of a breast implant,
    said fluid chambers being interconnected when implanted, such that fluid can be exchanged between the first and the more than two or second fluid chambers so as to change their respective fluid content,
    wherein two or more of said second fluid chambers are adapted for implantation within the human body remote from the breast implant so as to form a reservoir for the at least one first fluid chamber,
    the breast implant system further comprising at least one conduit between the remotely implantable more than two second fluid chambers and the at least one first fluid chamber for fluid exchange between the first and the more than two second fluid chambers.

7. The breast implant system of claim 6, comprising individual conduits between the two or more second fluid chambers and the at least one first fluid chamber for individual fluid exchange between the first and second fluid chambers.

8. A breast implant system, comprising
    a plurality of chambers including
    at least one first fluid chamber,
    at least one second fluid chamber,
    said first and second fluid chambers being adapted for implantation in the human body with the at least one first fluid chamber forming part of a breast implant,
    said fluid chambers being interconnected when implanted such that fluid can be exchanged between the first and second fluid chambers so as to change their respective fluid content,
    wherein at least one of said at least one second fluid chamber is adapted for implantation within the human body remote from the breast implant so as to form a reservoir for the at least one first fluid chamber,
    the breast implant system further comprising at least one conduit between the remotely implantable second fluid chamber and the at least one first fluid chamber for fluid exchange between the first and second fluid chambers, and at least one third chamber, wherein the at least one third chamber is isolated from the first and second fluid chambers.

9. The breast implant system of claim 8, wherein the at least one third chamber forms part of the breast implant and contains a compressible fluid, and wherein the first and second fluid chambers contain an incompressible fluid, the arrangement being such that fluid exchange between the first and second fluid chambers results in a change of pressure within the at least one third chamber, thereby causing a change of volume of the breast implant.

10. The breast implant system of claim 1, wherein at least one of said at least one second fluid chamber is adapted for implantation in the patient's abdominal cavity or inside the patient's chest area or outside the thorax under the minor pectoralis muscle or between the major and the minor pectoralis muscles.

11. The breast implant system of claim 10, wherein the surface-to-volume ratio of said second fluid chamber adapted for implantation outside the thorax is larger than the surface-to-volume ratio of the at least one first fluid chamber of the breast implant.

12. The breast implant system of claim 1, wherein at least one of said at least one second fluid chamber is adapted to be implanted subcutaneously such that fluid can be exchanged at least between the first and second fluid chambers by manually compressing the one or the other fluid chamber, thereby urging fluid to flow from the one fluid chamber into the other fluid chamber.

13. The breast implant system of claim 12, wherein more than one first fluid chamber forms part of the breast implant and wherein more than one second fluid chamber is adapted to be implanted subcutaneously such that fluid can be exchanged between the first and second fluid chambers by manually compressing the one or the other second fluid chamber, thereby urging fluid to flow from the one or the other second fluid chamber into one or more of the first fluid chambers.

14. The breast implant system of claim 12, wherein the at least one valve includes a pressure relief valve which opens at a predetermined pressure.

15. The breast implant system of claim 14, wherein the pressure relief valve is a two-way pressure relief valve which opens in the one or the other direction depending upon the side where the predetermined pressure is applied.

16. The breast implant system of claim 1, further comprising a pump adapted for pumping fluid between the first and second fluid chambers.

17. The breast implant system of claim 1, further comprising an energy source for supplying energy directly or indirectly to at least one energy consuming part of the system.

18. The breast implant system of claim 17, wherein the energy source comprises a wireless energy transmitter adapted to wirelessly transmit energy from outside the patient's body to the at least one energy consuming part.

19. The breast implant system of claim 1, further comprising a control unit adapted to directly or indirectly control one or more elements of the system.

20. The breast implant system of claim 1, wherein the control unit is adapted to control actuation of a pump.

\* \* \* \* \*